United States Patent [19]

Michaels

[11] Patent Number: 4,968,314
[45] Date of Patent: Nov. 6, 1990

[54] SURGICAL APPARATUS
[75] Inventor: Jonathan A. Michaels, Wembley, England
[73] Assignee: University College, London, England
[21] Appl. No.: 254,588
[22] Filed: Oct. 7, 1988
[30] Foreign Application Priority Data
  Oct. 7, 1987 [GB] United Kingdom ............... 8723476
  Apr. 20, 1988 [GB] United Kingdom ............... 8809325
[51] Int. Cl.$^5$ ...................... A61B 17/36; A61N 5/06
[52] U.S. Cl. .................................. 606/007; 606/15; 128/397
[58] Field of Search .............. 128/303.1, 395, 397, 128/398, 362; 606/7, 13–15

[56] References Cited
U.S. PATENT DOCUMENTS

| 4,418,688 | 12/1983 | Loeb ............................ 128/398 |
| 4,551,129 | 11/1985 | Gleman et al. ............... 128/303.1 |
| 4,627,435 | 12/1986 | Hoskin ......................... 128/303.1 |
| 4,641,912 | 2/1987 | Goldenberg .................. 128/398 |
| 4,686,979 | 8/1987 | Gruen et al. ................. 128/303.1 |
| 4,718,423 | 1/1988 | Willis et al. .................. 128/634 |
| 4,760,845 | 8/1988 | Kovalcheck .................. 128/398 |
| 4,773,413 | 9/1988 | Hussein et al. .............. 128/398 |
| 4,776,340 | 10/1988 | Mavan et al. ................ 128/634 |
| 4,785,806 | 11/1988 | Deckelbaum ................ 178/303.1 |
| 4,844,062 | 7/1989 | Wells .......................... 128/303.1 |
| 4,860,743 | 8/1989 | Abela .......................... 606/7 |

Primary Examiner—Lee S. Cohen
Assistant Examiner—John C. Hanley
Attorney, Agent, or Firm—William E. Cleaver

[57] ABSTRACT

Surgical apparatus which includes a waveguide, for example an optical fibre, through which laser energy is applied to tissues for such purposes as ablation of atheroma, destruction of calculi and lithotripsy. The optical fiber is provided with an end-piece through which it passes, and terminates flush with the distal end in the end-piece. For various applications at least the tip of the end-piece may be made either highly reflective or highly absorptive of the laser radiation. A balloon catheter may be fitted over the optical fibre. The end-piece may be provided with sensing means.

11 Claims, 4 Drawing Sheets

SURGICAL APPARATUS

Background of the Disclosure

There are many medical applications in which it is desired to deliver laser energy through a fibre-optic or similar waveguide device (disposed in a body cavity) into soft tissues, or into a viscus, for treatment or diagnosis. These include the ablation of tissue such as tumours or atheroma, the destruction of calculi in the biliary tree, bladder or ureters, the heating for coagulation of bleeding vessels, and the treatment of tumours and other lesions by photodynamic therapy or hyperthermia. The lasers used may produce either pulsed or continuous-wave light of wavelengths ranging from the ultra-violet to the far infra-red.

When optic fibres are used they comprise a core of transparent material of a first refractive index with a cladding of material of a higher refractive index. Both core and cladding are fabricated from suitably doped silica glass. In addition, most fibres have an outer layer which adds to the strength of the fibre and protects its surface. This outer layer is referred to as the buffer. In some cases an outer protective sheath, usually in the form of a spiral or braid of stainless steel wire, may be added. Glasses are not, in general, transparent in the far infra-red region, and tubular waveguides are being developed for use in that region.

For angioplasty, silica glass optic fibres are suitable and are used with a wide range of wavelengths. The choice of fibre diameter is a compromise between the flexibility necessary to enable it to be introduced to the site at which it is required, and the requirements of mechanical strength and safety and power-handling capacity. Fibres of the materials commonly employed, with a diameter of more than about 600 micro-meters, are not flexible enough for percutaneous introduction into the larger vessels, and for the smaller distal leg vessels or coronary vessels a fibre of not more than 200–300 micro-metres diameter is required. Loss of laser power through the cladding also sets a limit to the minimum radius of curvature through which the fibre can be bent, and this, too, depends on the fibre diameter.

The ends of bare optical fibres of the dimensions mentioned are sufficiently fine and sharp to penetrate the wall of a viscus instead of passing smoothly along its lumen, and various methods have been tried to overcome this sharp edge problem.

In one such solution a metal end-cap has been fitted over the tip of the fibre. With the foregoing technique, the energy is then entirely converted to heat, and it is contact with the hot end which causes ablation. Short pulses cannot be used with the metal end-cap, because of the very high temperatures that are produced momentarily at the junction of the metal with the fibre, and also, because the metal has a high thermal conductivity, the whole of the metal tip is heated, causing damage to the walls of the body cavity or blood constituents.

In another proposed solution a sapphire tip has been used. The surface of a highly polished sapphire is difficult to bond to a glass fibre, and accordingly secure junctions between optic fibres and sapphire cannot be produced. For this reason the sapphire is mounted on a metal connector fixed to a catheter through which the fibre is passed. Such a device is thick and relatively inflexible, making it unsuitable for use in small blood vessels or where it is required to pass a balloon catheter over it. Also, it is difficult to maintain the position of the fibre with respect to the sapphire, and the junction becomes contaminated with charred blood. Since the refractive index of sapphire is higher than that of the fibre there is a heat loss at the interface and the metal tip becomes heated, with the disadvantages mentioned above.

Ball-tipped or lens-tipped devices have been proposed, and these can be readily formed merely by melting the tip of a silica-glass optic fibre. There are, however, problems with respect to the mechanical strength and safety of such tips, particularly after exposure to heat, laser light and the mechanical stresses of clinical use. A supporting structure, for example a metal collar, can be employed with such tips, but this arrangement becomes heated in use, again with the disadvantages mentioned above.

SUMMARY OF THE DISCLOSURE

In the case of vascular tissue exposed to near infra-red radiation from a neodymium-YAG laser, it has been shown that 30%–40% of the incident light is back-scattered from the surface being irradiated. This back-scattered light may also cause damage to tissues or to the device itself. It has been demonstrated, by theoretical modelling, and also with the aid of a thermal camera, that this back-scatter radiation causes heating of a modified fibre tip.

In the present invention, which is defined in the claims appended hereto, use is made of this back-scattered radiation. Instead of an end-cap, the waveguide has an end-piece in the form of a bead, with the waveguide passing right through the end-piece and terminating at its distal end. In this arrangement the waveguide can come close to, or into actual contact with, the tissue to be treated. Because there is no interface within the tip at which any part of the laser light is dissipated, an optic fibre used in this way is capable of transmitting as much energy as a bare fibre. The end of the fibre should be flush with the tip of the end-piece. If the tip protrudes it is likely to cause tissue damage, while if the tip is not flush a recess will be formed which acts to accumulate charred fibrin and blood cells which interferes with the laser light being transmitted.

For angioplasty, the end piece with the flush fibre-tip is preferably used with a pulsed laser. It has been shown that by using pulses which are short compared with the thermal relaxation time of the irradiated tissue, it is possible to vaporise a small region of tissue without much transfer of heat to the surrounding tissues. For such applications as ablation, a highly reflecting material, such as polished metal, is most suitable for the end-piece. By using the polished metal for the end piece the back-scattered light is reflected back again directly into the region being treated. Stainless steel is a suitable material to fabricate a polished end-piece.

In applications where some heating is required, such as for haemostatis, radiation (which penetrates further into the tissues), such as red or infra-red, is preferred. It is also preferable in such applications to make the end-piece of a material which absorbs radiation at the laser wavelength. The radiation back-scattered from the tissue being treated will be incident on the front surface of the end-piece, and the end-piece is in contact with the tissue being treated. By using material which is a poor thermal conductor, such as a ceramic material, for the end-piece, and applying power at a low level, or for periods which are short compared with the time required for conduction within the end-piece, high temperatures can be produced at the waveguide tip and a small surrounding region at the front surface of the end-piece without the excessive heating at the sides and back.

The device may also include an additional optical fibre as a sensing device, allowing the intensity of radiation at the end-piece to be monitored. The sensing device may provide information for diagnostic purposes, or it may form part of a feedback loop for controlling the laser output.

In certain applications the mechanical strength of the attachment of the end-piece may be the main concern. For example, in lithotripsy, where the end-piece may be required to shatter a calculus in contact with the tip the mechanical strength is of concern. In these cases a fibre may be used which is sheathed with a spiral or braid of wire, for example of stainless steel, and the end-piece may be of metal attached to the sheath.

A single device comprising an optic fibre and end-piece may be used for different purposes, since the fibre should be capable of transmitting a large range of wavelengths and pulse energies. For example, a pulsed laser at a slow repetition rate with a high pulse energy may be used for cutting or ablation, and the laser may then be switched to continuous-wave or low-energy rapid-pulse output for coagulation. Such an arrangement has application in many areas of surgery.

The invention will be further described with reference to the accompanying drawings, in which FIG. 1 shows diagrammatically the apparatus of the present invention;

FIGS. 4(a) and 4(b) show the use of a wire for guiding the fibre into position in a blood-vessel.

Figure 1:
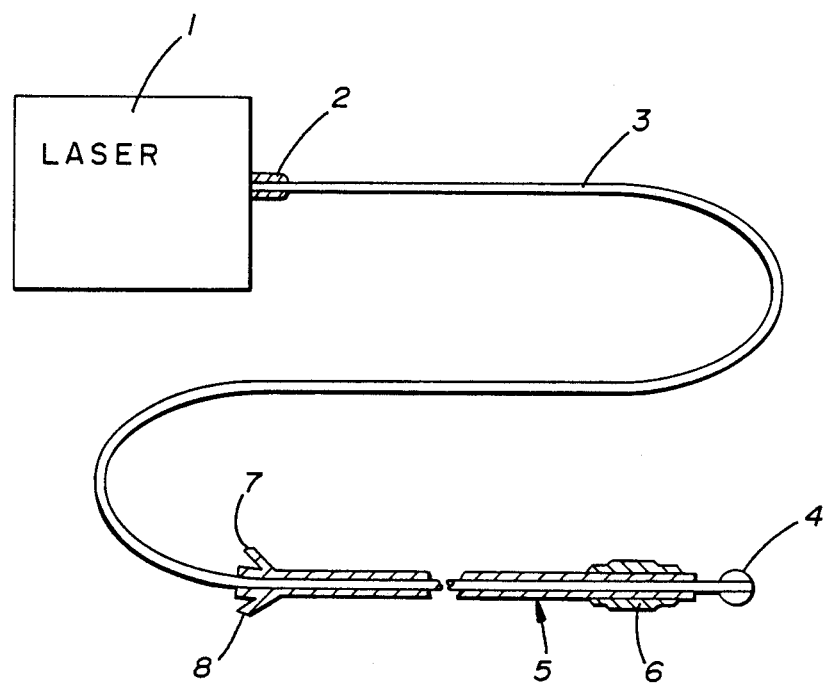

Referring first to FIG. 1, the apparatus comprises a laser 1 coupled by a connector 2 to a waveguide 3, which, in a preferred embodiment is a fibre of silica glass with a doped silica glass cladding and a biologically inert plastic sheath. The fibre terminates in an end-piece 4, which will be described more fully below in connection with FIG. 2.

A balloon catheter 5 is mounted on the fibre 3 so as to be free to slide along it. This has an inflatable balloon 6, and is provided with a pair of channels 7, 8 for inflation and for the introduction of perfusion saline.

Figure 2:
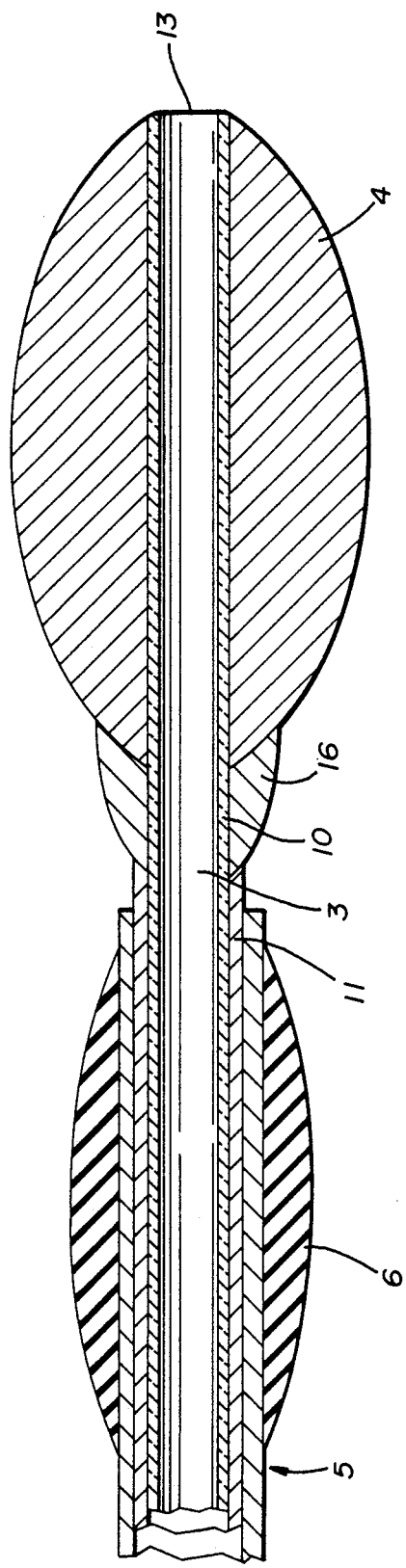
FIG. 2 is an enlarged section of the tip of the optic fibre and its end-piece, with a balloon catheter in place on the fibre.

FIG. 2 is a section on a larger scale of the fibre tip and a portion of the balloon catheter. The fibre 3 has an outer buffer 10, over which is a sheath of braided stainless steel wire 11. The end of the fibre passes into a metal end-piece 4 (which is in the form of a rounded bead), and terminates at 13, flush with the extremity of the bead. The bead is secured to the sheath 11 by adhesive or solder 15 of a composition which is not irritant to body tissues. The balloon catheter, (the balloon portion 6 of which is shown diagrammatically in the Figure), slides over the fibre 3 and its sheath 11.

In use of the present invention for angioplasty, for example, it is inserted into the artery and fed forward until it reaches the atheratomatous obstruction it is desired to treat. The rounded tip comprises of the polished metal bead surrounding the fibre end ensures that the procedure can be done with minimal risk of damaging the artery wall. Brief pulses of energy from the laser, preferably of less than 1 millisecond duration, are then transmitted down the fibre, and emerge at the fibre end 13 to cause ablation of the tissue in contact with this end. A substantial proportion of this energy is back-reflected and strikes the surface of the polished metal bead in the region 14 immediately surrounding the fibre tip. Since the end-piece is of polished metal and reflects the laser light almost all of this reflected energy is reflected back again into the tissues being ablated particularly in the region immediately surrounding the fibre tip, and scarcely any is dissipated in heating the end-piece.

Angioplasty may be carried out using a neodymium-YAG laser having a wavelength of 1064 nanometers, and using pulses of 100 microsecond duration at a repetition rate of 10 Hz. Suitable pulse energies are in the range of 0.3–0.7 J per pulse. For angioplasty, the most useful fibres are of diameters ranging from 200 to 600 micrometers with end-piece diameters of 1–2 mm. Of these, the larger sizes would be suitable for femoral or iliac vessels, and the smaller sizes for coronary arteries, or leg arteries below the knee.

For lithotripsy a pulsed dye laser operating in the visible region and producing pulses of about 1 microsecond would preferably be used.

In the apparatus so far described the fibre may either be cemented into the end-piece, or it may be friction fitted. If friction fitted, it may be made removable from the end-piece and sheath, so that it may be replaced by a thin guide-wire, and another device, such as a different size of balloon catheter or dilator, may be inserted along the guide-wire.

For some purposes, for example haemostatis or the hyperthermic treatment of tumours, the device of the invention may be so designed and proportioned that it can readily be introduced into the body through an endoscope, or through a cannula.

In an alternative form of the apparatus the braided sheath is not employed, and the end-piece is cemented directly to the fibre, with the balloon catheter, if one is used, sliding directly over the fibre sheath. This provides a more flexible structure, and allows a rather thicker fibre to be used.

For use in applications such as thermal coagulation, where a thermal effect at a lower temperature is required instead of ablation, at least the tip region 14 may be of a material which absorbs the laser energy instead of reflecting it. By this means the tip region itself becomes heated and is effective in causing coagulation. Preferably in this case the body of the end-piece is of a poor thermal conductor, so helping to concentrate the heating in the region immediately surrounding the tip, and avoiding excessive heating of the rear part of the end-piece, where it might cause undesired effects. In this case, also, a rapid pulse repetition rate, or a continuous wave laser, may be appropriate.

The end-piece may be provided with means for sensing the energy supplied at the fibre tip. By such means the operator may ensure that the apparatus is functioning correctly, or it may provide a feedback path for control of the energy supplied. The means may comprise a thermocouple or other measuring device, or it may consist of a second optical fibre having its extremity in juxtaposition to the main fibre. The energy sensor may form part of a feedback circuit for controlling the operation of the laser.

Figure 3:
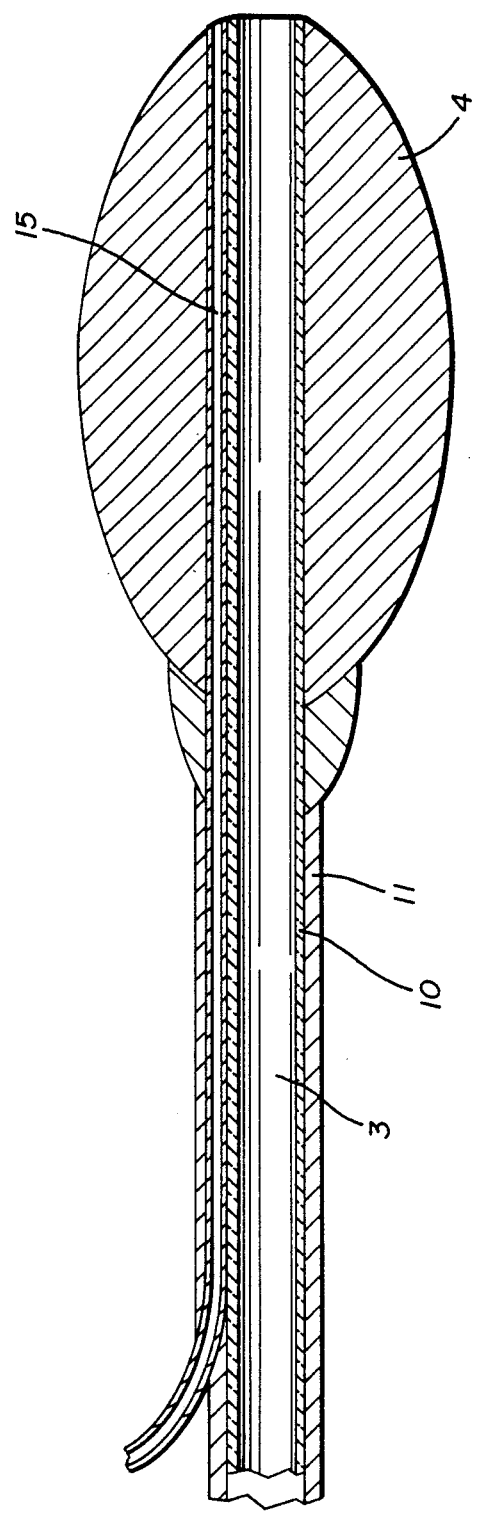
FIG. 3 is an enlarged section of a modified form of fibre tip.

FIG. 3 shows, in section, an end-piece of a generally similar form to that of FIG. 2, but provided with such a sensing fibre. In FIG. 3 the main fibre 3 conveying energy from the laser for ablation has a second fibre 15 lying alongside it, and terminating closely adjacent to its tip 13. This fibre serves for sensing purposes, leading back to an indicting instrument (not shown in the drawing). When the apparatus is in use the absence of a reading on this instrument, or the occurrence of readings different from those normally obtained, will alert the operator to the need for adjustment.

In an alternative arrangement, not shown in the drawings, a guide wire with a curved flexible tip passes through a catheter alongside the fibre and through a channel drilled through the bead. The guide wire is used to guide the bead and fibre through the vessel in a known manner, and may be withdrawn once the fibre has been correctly positioned.

FIGS. 4(a) and 4(b) show an arrangement in which a guide wire 17 passes through a series of guides 18 along the fibre and then through a channel drilled through the bead 4. The end of this wire is enlarged, as shown at 20, so that the bead 4 cannot pass over it. By altering the tension applied to the wire and rotating the device it may be guided under X-ray fluoroscopy so as to follow the curvature of a blood-vessel, or to direct the fibre tip along a desired branch of the vessel. The wire, with its enlarged head, serves also as an additional safeguard against accidental detachment of the fibre tip.

When a channel has been made through a blockage in a blood-vessel and the tip of the device has passed beyond it, the bead and optic fibre may be withdrawn, leaving the wire in place. A balloon catheter may then be inserted over the guide wire to enable balloon angioplasty to be carried on in the usual way.

I claim:

1. A device to be used in surgical procedures whereby the wall tissue of a body cavity is atraumatically spread apart is response to inserting said device therein and whereby laser light energy is employed through said device in effecting such surgical procedures, comprising in combination:

A waveguide having at least a flat tip end and an opposite end arranged to be coupled to a laser light source, said waveguide being capable of transmitting laser light energy from said opposite end through said flat tip end of said waveguide; an optically end piece opaque having a bulbous shape with a first end and a distal end and with an aperture passing through said first and distal ends, said end piece having its aperture fitted over said waveguide and fixedly secured to said waveguide such that said distal end of said end piece is flush with said flat tip end of said waveguide wherein said bulbous shape of said end piece is further defined as having an outer peripheral surface having a continuously smooth arcuate contour extending at least from the aperture in said first end to a point of maximum width of said end piece with respect to a longitudinal axis of the waveguide whereby (1) the wall tissue of a body cavity will be atraumatically spread apart in response to the combination of said end piece and said flat tip end of said waveguide being passed into said body cavity, and whereby (2) tissue to be treated can be irradiated by light energy from a laser light source passing through said flat tip end without significant dissipation of laser light energy before such energy strikes the tissue to be treated.

2. A device according to claim 1 wherein said waveguide is an optical fibre.

3. A device according to claim 2 wherein said endpiece is formed of polished stainless steel.

4. A device according to claim 3 wherein there is further included a wire sheath means for coaxially encompassing said optical fibre.

5. A device according to claim 4 wherein said wire sheath means is attached to said end-piece.

6. A device according to claim 1 wherein there is further included a laser light source coupled to said opposite end of said waveguide.

7. A device according to claim 6 wherein said laser light source is a neodynium-YAG laser.

8. A device according to claim 7 wherein said laser delivers energy in pulses of less than one millisecond duration, with each pulse being of an energy sufficient to cause ablation of tissue.

9. A device according to claim 1 wherein said distal end of said end-piece is formed of a material which absorbs light energy.

10. A device according to claim 9 wherein said material is ceramic material.

11. A device according to claim 1 wherein said end piece is designed to reflect light energy which is backscattered from said tissue being irradiated whereby said end piece does not heat up to a degree to do damage to surrounding tissue.

* * * * *